(12) United States Patent
Manoach

(10) Patent No.: US 6,626,856 B2
(45) Date of Patent: Sep. 30, 2003

(54) SEMI-RIGID PELVIC COMPRESSION SPLINT FOR TRAUMA

(75) Inventor: Seth M. Manoach, New York, NY (US)

(73) Assignee: The Research Foundation of State University of New York, Albany, NY (US)

( * ) Notice: Subject to any disclaimer, the term of this patent is extended or adjusted under 35 U.S.C. 154(b) by 23 days.

(21) Appl. No.: 09/860,712

(22) Filed: May 18, 2001

(65) Prior Publication Data

US 2001/0047142 A1 Nov. 29, 2001

Related U.S. Application Data

(60) Provisional application No. 60/205,662, filed on May 19, 2000.

(51) Int. Cl.$^7$ .................................................. A61F 5/00
(52) U.S. Cl. ............................. 602/5; 602/4; 602/61; 128/875
(58) Field of Search .......................... 602/23, 27, 62, 602/65, 75, 4–5; 128/882, 898, 875; 119/850; 54/82; 482/111, 112, 142, 148; 446/220, 221

(56) References Cited

U.S. PATENT DOCUMENTS

| 4,577,622 A | * | 3/1986 | Jennings ..................... 601/134 |
| 4,580,555 A | * | 4/1986 | Coppess ....................... 602/23 |
| 5,383,893 A | * | 1/1995 | Daneshvar .................. 606/201 |
| 5,383,920 A | * | 1/1995 | Sikes ........................... 607/112 |
| 5,799,650 A | * | 9/1998 | Harris .......................... 128/96.1 |
| 5,830,168 A | * | 11/1998 | Finnell et al. |
| 5,893,368 A | * | 4/1999 | Sugerman ................... 128/898 |
| 6,065,166 A | * | 5/2000 | Sharrock et al. ............... 5/630 |
| 6,066,109 A | * | 5/2000 | Buser et al. ................... 602/23 |

* cited by examiner

Primary Examiner—Nicholas D. Lucchesi
Assistant Examiner—Lalita M. Hamilton
(74) Attorney, Agent, or Firm—Scully, Scott Murphy & Presser

(57) ABSTRACT

A pelvic compression splint for splinting support and compression of the pelvis. The pelvic compression splint includes: right and left plates to be positioned on the right and left sides, respectively, of the pelvis; right and left inner shells positioned between the right and left plates, respectively, and the right and left side of the pelvis; and a support member for supporting the right and left plates and right and left inner shells compressively against the right and left sides of the pelvis.

9 Claims, 8 Drawing Sheets

SEMI-RIGID PELVIC COMPRESSION SPLINT FOR TRAUMA

CROSS-REFERENCE TO RELATED APPLICATIONS

This application is a conversion of provisional application No. 60/205,662 filed May 19, 2000.

BACKGROUND OF THE INVENTION

1. Field of the Invention

The present invention relates generally to compression splints for trauma and, more particularly, to a semi-rigid pelvic compression splint.

2. Prior Art

Pelvic compression splints of the prior art are typically fabricated from a solid piece of fabric or other material. While these splints have their advantages in order to ensure that the providers can see and access the anterior abdomen, pelvis, and ano-genital regions, the splint must be disengaged. Furthermore, these pelvic compression splints of the prior art cause compressive forces to be applied to the soft anterior abdominal/pelvic wall and not to the bony pelvis itself where it is most needed.

Each device that is used to compress and stabilize the pelvis has unique attributes and flaws. The principal devices in common use are the military and anti-shock trousers (MAST pants), and a variety of external frames that use pins to attach to the pelvis. The semi-rigid pelvic compression splint of the present invention is designed to combine the non-invasiveness and adjustability of the MAST garment with the medially-directed compression vectors and limb, femoral and anterior abdomino-pelvic exposure of the C-clamp, Pelvic Stabilizer and External Fixator.

MAST pants (military anti-shock trousers or the PASG (pneumatic anti-shock garment) were first used in the Vietnam era for shock resulting from military injuries. They are nylon pant suits with inflatable compartments. They are fit around the patient's legs and torso and extend from the ankle to the lower rib cage. They are closed with Velcro and the inflatable compartments are filled from inferior to superior. There are compartments running up the circumference of each leg, and a large compartment is located over the anterior pelvis and abdomen that extends to the rib cage. The original purpose of the MAST pants was to force blood out of the extremities, pelvis and lower abdomen and into the central circulation supplying the brain and cardiopulmonary system. This process was referred to as "auto-transfusion", and it was initially believed that the pants worked through this mechanism to restore effective central circulation volume and save lives. It is now believed that blood pressure increases related to the MAST pants result from increased afterload, and that the increased intra-abdominal pressure generated by the MAST pants may "theoretically" reduce some bleeding in this area.

Whatever their affects on hemodynamics, the use of MAST pants has been called into question during the last ten years. Studies have shown that the device does not decrease morbidity and mortality in trauma-related hemorrhagic shock, and that it may be detrimental to patients with associated chest trauma. As a result, the routine use of MAST pants by EMS units has been largely phased out in the United States. Fortuitously, as this de-emphasis of MAST-pants application occurred, they were found to be effective in stabilizing and compressing the fractured pelvis in the EMS and ED setting. As a result MAST pants have had a second life as a limited part of certain pre-hospital and emergency department pelvic trauma resuscitation protocols.

Unfortunately, use of the MAST pants in the pelvic fracture is limited by their many disadvantages. They are only sparingly used in America and a 1995 study reported that only about 10% to 20% of British trauma centers used them, respectively, for pre-hospital and in-patient care. There are many reasons for this. They are somewhat difficult to place on a patient because they cover such a large part of the body, have many closures, and must be completely opened before the patient can be placed in them. Once the pants are fitted, they cover the entire area of the lower limbs, pelvis and abdomen up to the rib cage. The coverage of the legs is unwanted because it prevents assessment of the lower limbs, and compression of the lower limbs has been found to cause compartment syndromes.

Even if MAST pants could be used without attaching the leg pieces, the abdomino-pelvic component would still obscure the entire abdomino-pelvic region up to the rib cage. As noted above, restricting visibility and access to this area is a major disadvantage in trauma care because about half of all pelvic fracture patients also have serious intra-abdominal injuries that must be assessed in a timely fashion. These problems are further complicated by the fact that opening the pants must be done very slowly because there is often a large drop in blood pressure caused by the rapid decrease in afterload associated with garment removal.

Simply trimming MAST pants to a size that conforms to pelvic area would not make them ideal for pelvic compression and stabilization—another shortcoming of the MAST pants is that the compression vector of the abdomino-pelvic component is anterior to posterior. The pants use a large anterior inflatable compartment that compresses the anterior abdomen, increasing intra-abdominal pressure and decreasing the volume of the abdomen and pelvis. Any medially-directed compression is secondary to the dominant anterior-posterior compressive force of the device. Primary AP compression is not optimal for achieving partial reduction, compression, and stabilization of sacro-iliac disruption and pubic symphysis diastasis, and all recently developed invasive external frames primarily employ medially-directed compression vectors. While increasing intra-abdominal pressure may have some theoretical benefit, it has more physiologic costs than medially-directed compression. Both human and animal studies have shown that MAST pants reduce diaphragmatic excursion and compromise respiratory mechanics in critically ill patients. They may also worsen left ventricular function, especially in those with pre-existing heart disease. In addition, AP compression compromises skin integrity over crucial anterior and posterior operative approaches to the pelvis, impeding definitive repair of the injury. Finally, there is no way to achieve anterior-posterior compression without completely obscuring at least part of the anterior abdomen and pelvis.

The history of the MAST pants is interesting in this light, because limb and AP compression over the soft anterior abdomino-pelvic wall does seem to be more likely to squeeze blood into the upper torso than medially directed compression of the relatively rigid contours of the bony pelvis. Unfortunately, as noted above, the autotransfusion/increased afterload function of the device has not been found to be effective for improving outcomes in trauma. The later discovery that the device is helpful in pelvic fractures was fortunate, but the fact that MAST pants were not designed for pelvic stabilization has given them numerous features (described above) that severely limit their use in the multiply-injured blunt trauma patient with a potential pelvic fracture.

The invasive external pelvic compression/stabilization devices of the prior art include the External Fixator, C-Clamp, and Pelvic Stabilizer. The term "invasive" is used to mean that in order to use any of these devices, an orthopedic surgeon, or other specially trained provider must incise the patient's skin, dissect through fascial and/or muscle layers and place a pin into the bony pelvis.

These devices were all designed to stabilize and compress the pelvis before definitive operative repair can be done. Unlike the MAST pants, they were designed for this purpose and primarily provide medially-directed compression of the pelvis while allowing the trauma team to have access to the abdomen and extremities. As briefly mentioned above, all work on the same principle: an external compression frame is connected to the pelvis by means of transcutanous pins that are surgically placed into the iliac wings or posterior ileum. The frame is then adjusted to compress/stabilize and possibly reduce the pelvic disruption. The frame itself can then be swung inferiorly or superiorly to facilitate access to the abdomen or lower limbs.

The frames themselves vary. The External fixator is generally favored for open book fractures with pubic symphysis diatheses. Its pins are placed in the iliac wings, and it is thought to be less useful in posterior disruptions of the sacroiliac joints. The Pelvic Stablizer is also pinned to the iliac wing but it is designed to be more useful than the EX-fix for SI joint disruption. The Pelvic Anti-Shock Clamp (C-Clamp) is pinned to the posterior ileum and it applies medially-directed compression to the sacro-iliac joint in order to stabilize posterior ring disruptions. Like the MAST pants, External Fixators have been shown to be effective in treating pelvic fractures. The posterior devices have only been used for a brief period of time, but both show promise in the stabilization of bony structures and control of hemorrhage.

The external compression frames have two major advantages—they are effective in compressing pelvic fractures, and they allow unrestricted access to the abdomen or lower extremities. Despite this, use is severely limited by the need to have an orthopedic surgeon present who can dissect through skin and muscle and properly place a pin in bone. Obviously, the required time and talent for this procedure is not available in the pre-hospital context, and rarely if ever available in a community hospital that functions in the trauma system as a point for resuscitation, stabilization, and transfer.

Even at level one trauma centers, the invasive devices are rarely used. Even with the resources of level one trauma centers, multiple blunt trauma patients are difficult to stabilize. In the initial stages of management, work is concentrated on establishing an airway, obtaining adequate IV access, placing chest tubes, performing an adequate secondary survey, and obtaining basic radiographs. At this point there are usually too many people and too much going on around the bed to accommodate an orthopedic team that needs to closely inspect the pelvis, antiseptically prepare the skin over the pelvis, and place these devices. Later in the resuscitation the priority becomes determining if dangerous intra-abdominal or intracranial injuries are present. Finally, in the situation in which an external fixator or C-Clamp is desired, the in-house orthopedic staff often consists of residents who are not as highly skilled in performing the procedures as attending orthopedic traumatologists with expertise in this area. Even with skilled staff there would be other costs of placing the frames. There is a risk of pin tract infection complicating later open reduction and internal fixation, and time lost for other emergent procedures, such as diagnostic peritoneal lavage, CT scan, laparotomy and pelvic angiography.

SUMMARY OF THE INVENTION

Therefore, it is an object of the present invention to provide a semi-rigid pelvic compression splint for trauma that provides rapid, simple, non-invasive pre-hospital and ED compression and stabilization of pelvic injuries which is able to be partially assembled beforehand, slid under the patient, and rapidly closed anteriorly without obscuring abdominal and pelvic anatomy and injury.

It is also an object of the present invention to provide a semi-rigid pelvic compression splint for trauma that covers only an area of the body that needs to be stabilized in pelvic fractures and preserve access to the femoral triangles, lower limbs, and anterior pelvis and abdomen. Their adjustment and closeness of fit is a matter of tightening adjustable straps, placing foam-lined plastic splints against each lateral pelvis, and filling inflatable compartments.

The semi-rigid pelvic compression splint for Trauma is a new device that combines the best features of the MAST pants, External Fixator, Pelvic Anti-shock Clamp, and Pelvic Stabilizer. It is an inexpensive, completely non-invasive, rapidly-applied splint that will provide pelvic compression and stabilization at the sacro-iliac joint and the pubic symphysis. No specialized training is required to apply the splint, and it can be placed during pre-hospital, emergency department, OR or ICU care. Even when applied and fully engaged, the splint will allow visualization of and access to the ano-genital and femoral areas, anterior abdomen and pelvis, and lower limbs. It has no deleterious effects on cardio-pulmonary mechanics. The semi-rigid pelvic compression splint has an adjustable attachment and compression system, can be left in place during laparotomy, and is designed to minimize skin complications.

Relative to MAST pants, the semi-rigid pelvic compression splint of the present invention is designed to be easier and faster to place on the patient during the transport and resuscitation process. It allows the physician to see and access the anterior abdomen and pelvis, and provides the medially-directed compression vectors most likely to achieve stabilization, compression and partial reduction of pubic symphysis diastasis and sacro-iliac disruption (again, all the new invasive external frames provide primarily lateral to medial and not AP compression). It can be used in the ED, OR, CT or ICU environments, and is less likely than the MAST pants to cause skin breakdown over potential operative sites for definitive pelvic repair.

Accordingly, a pelvic compression splint for splinting support and compression of the pelvis is provided. The pelvic compression splint comprises: right and left support members to be positioned on the right and left sides, respectively, of the pelvis; and a support means for supporting the right and left support members compressively against the right and left sides of the pelvis.

Preferably the pelvic compression splint further comprises right and left cushions positioned between the right and left support members, respectively, and the right and left side of the pelvis. The right and left cushions preferably further have a concavity to fit the contours of the right and left sides of the pelvis, respectively. Preferably, at least one of the right and left cushions further comprises an inflatable compartment for applying further and varying compression against the right and left sides of the pelvis. The inflatable compartment preferably further comprises a pump and valve system for pressuring the inflatable compartment and releasing pressure therefrom, respectively.

The support means preferably comprises a sling fastened at each end to the support plates by a first plurality of straps, the support means further having a fastening means for maintaining the support plates and inner shells compressively against the right and left sides of the pelvis. The fastening means preferably comprises a second plurality of straps, each of the second plurality of straps having a fixing means for fixing the straps to each of the support plates.

In a preferred implementation of the semi-rigid compression splint, the same comprises: right and left plates to be positioned on the right and left sides, respectively, of the pelvis; right and left cushions positioned between the right and left plates, respectively, and the right and left side of the pelvis; and a support means for supporting the right and left plates and right and left cushions compressively against the right and left sides of the pelvis.

BRIEF DESCRIPTION OF THE DRAWINGS

These and other features, aspects, and advantages of the apparatus of the present invention will become better understood with regard to the following description, appended claims, and accompanying drawings where:

DETAILED DESCRIPTION OF THE PREFERRED EMBODIMENT

Figure 1:
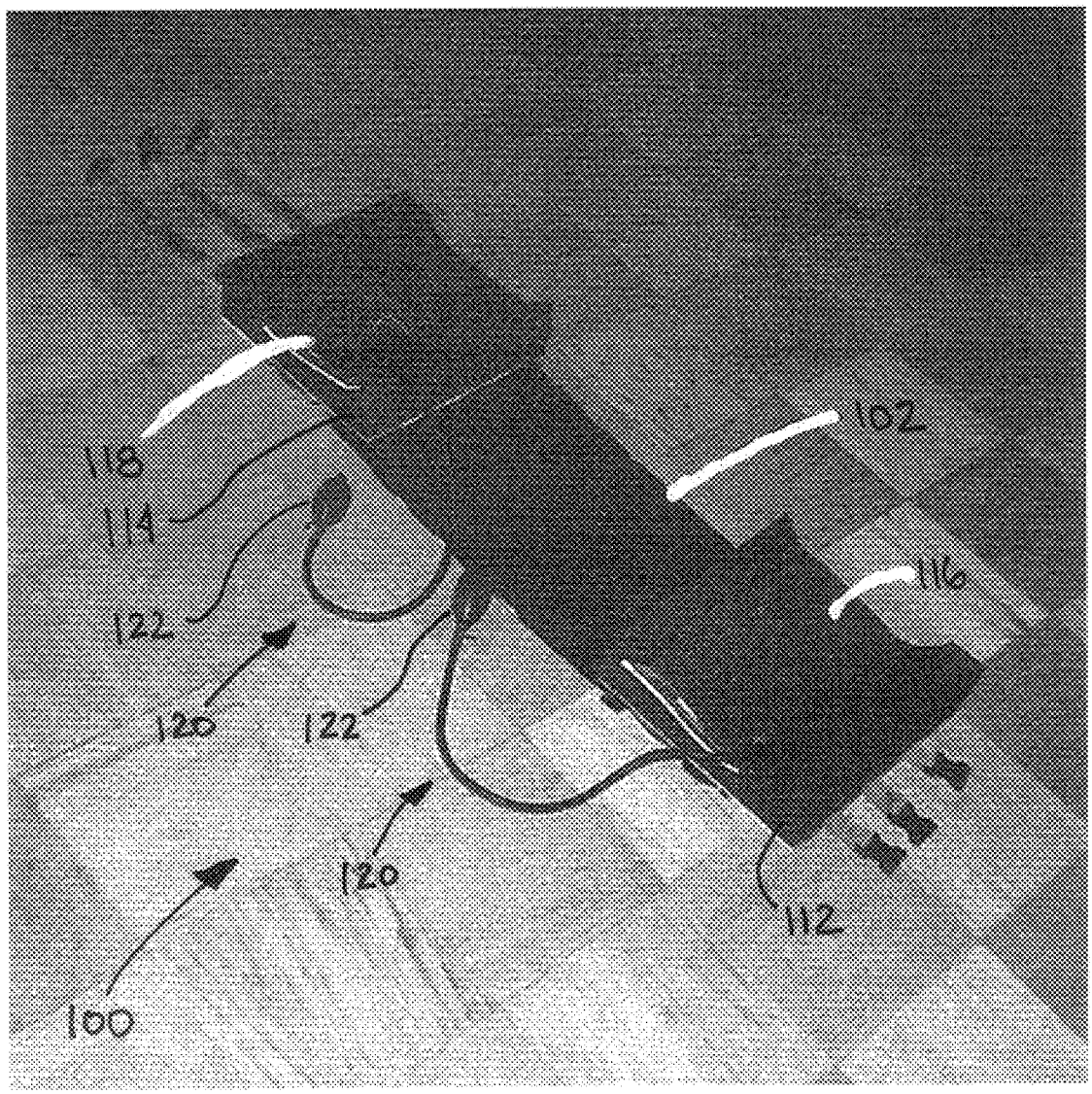
FIG. 1 illustrates a perspective view of the semi-rigid pelvic compression splint of the present invention in an open configuration.
Figure 2:
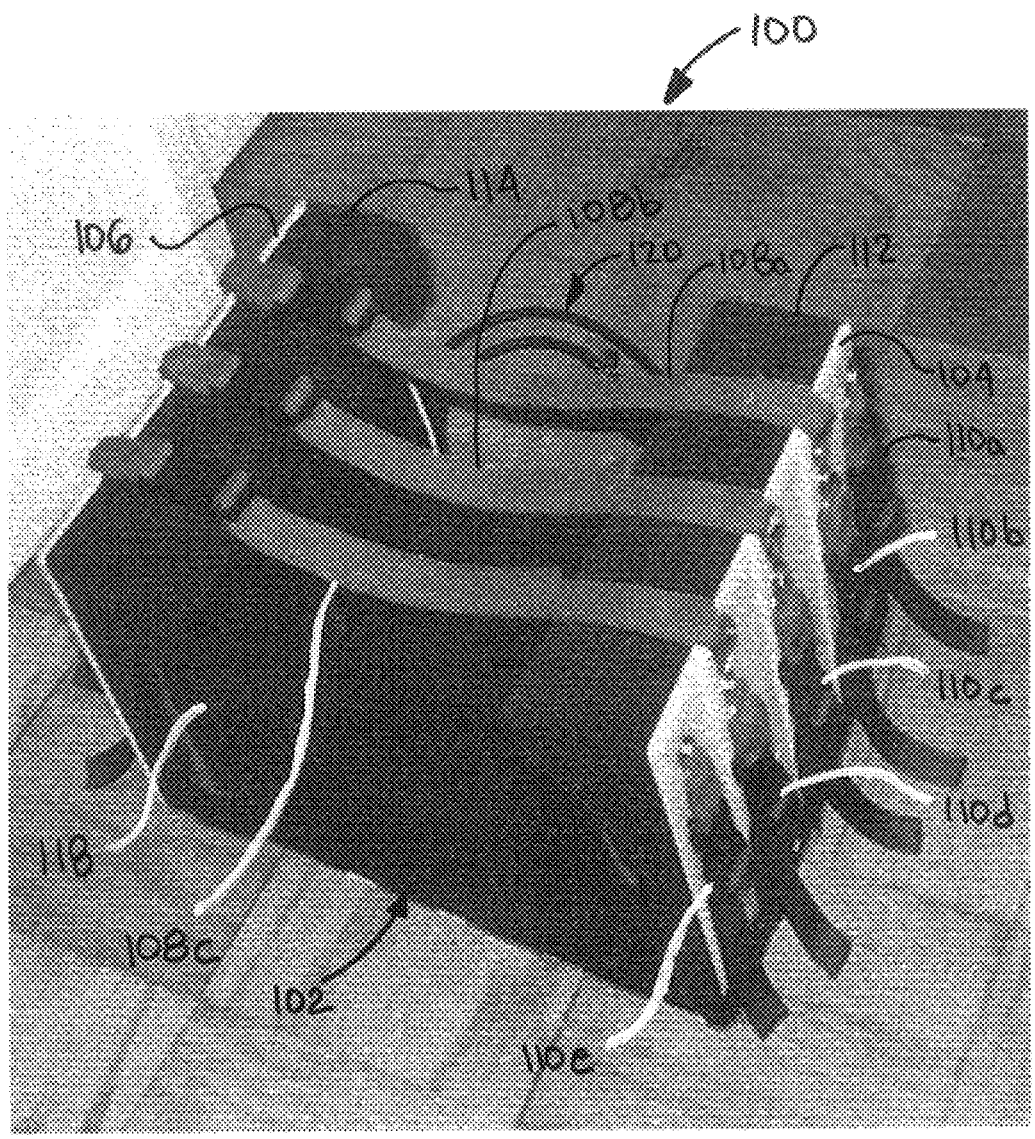
FIG. 2 illustrates a perspective view of the semi-rigid pelvic compression splint of the present invention in a closed configuration.

A semi-rigid pelvic compression splint of the present invention, generally referred to by reference numeral 100, will be discussed first in general and below with more specificity. The splint 100, when in an open position, as is shown in FIG. 1, is slid posterior to (under) the supine patient's buttocks, or is placed under the patient using the standard trauma log-rolling technique. A sling 102 and right and left lateral plates 104, 106 form the posterior and lateral aspects of the splint 100, as shown in FIG. 2. Three anterior straps 108a–108c connected to the anterior aspect of the external surface or one of the plates, such as the left lateral plate 106 and are passed superior to (over) the patient's lower abdomen and pelvis and attached to other lateral plate, in this case to the right lateral plate 104, as shown clearly in FIG. 3. Sling straps 110a–110e attach the posterior sling 102 to each of the lateral plates 104, 106 and the straps 108a–108c connecting the two lateral plates 104, 106 are adjusted to conform to the patient's pelvis. A system of cushions 112, 114 and air bladders 116, 118 as best seen in FIG. 1 are mounted on the internal side of each lateral plate 104, 106. After the splint 100 is in place on a patient, the air bladders 116, 118 are inflated to compress/stabilize the patient's pelvis. The straps 108a–108c and 110a–110e and air bladders 116, 118 may then be further manipulated to optimize the fit and function of the splint 100.

Figure 7:
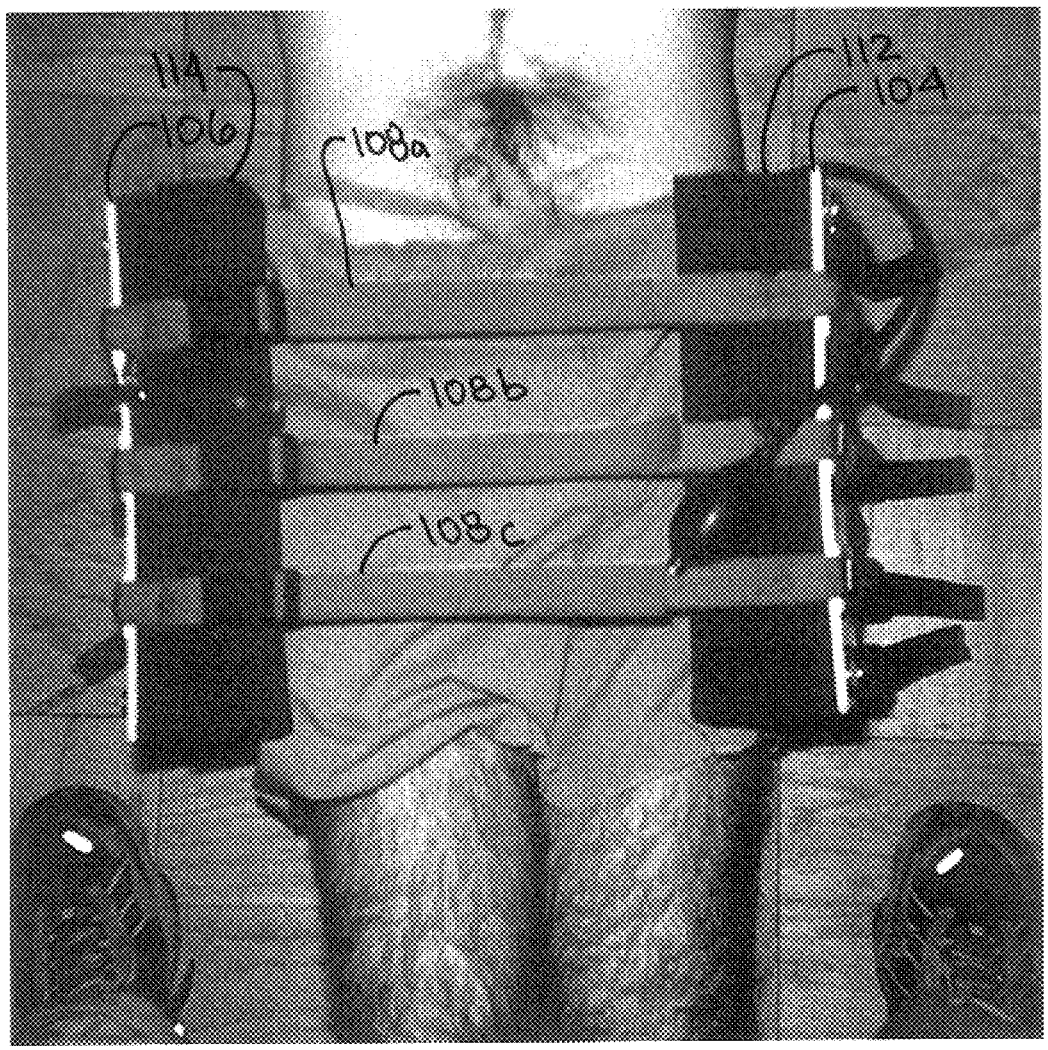
FIG. 7 illustrates the semi-rigid pelvic compression splint of the present invention shown fitted on a human subject.
Figure 8:
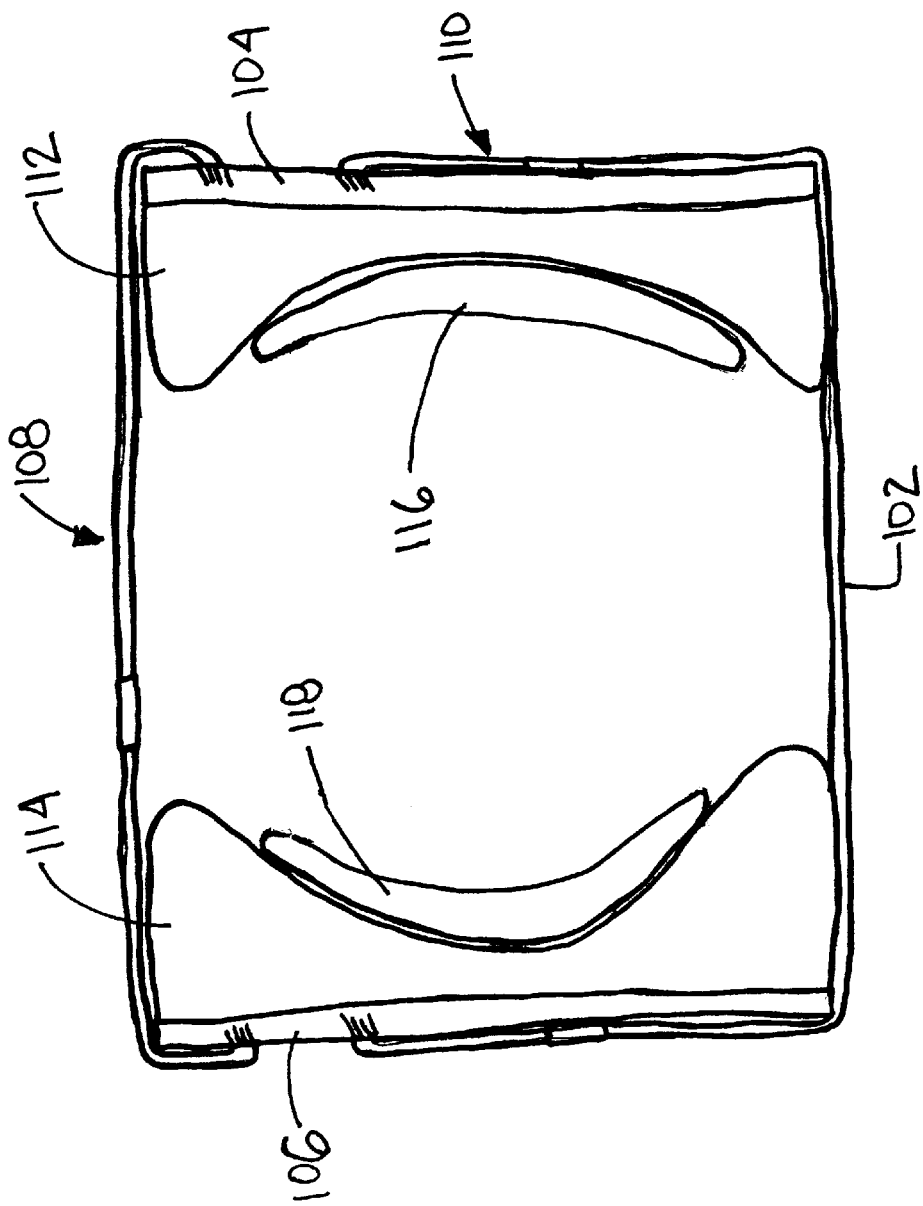
FIG. 8 illustrates a schematic side view of the semi-rigid pelvic compression splint of the present invention showing the "C" shaped right and left cushions.

As shown in FIG. 7, the lateral plates 104, 106 are designed to be of sufficient posterior-anterior height and rigidity such that the anterior straps 108a–108c project over, and are not in contact with the soft anterior abdominal/pelvic wall. In a prototype which has been actually reduced to practice, ribs (not shown) were used to reinforce the posterior-anterior rigidity of the lateral plates 104, 106, which were fabricated from acrylic. This feature, and the inherent openness of a strap system relative to a solid piece of fabric or other material ensure that the providers can see and access the anterior abdomen, pelvis, and ano-genital regions without disengaging the device. It is also extremely important to note that the design as a whole causes compressive forces to be applied to the bony pelvis itself and not to the soft anterior abdominal/pelvic wall.

Specific details of the splint 100 of the present invention will now be described with reference to FIGS. 1–8. As discussed above, the semi-rigid pelvic compression splint 100 of the present invention comprises a posterior sling 102, as shown separately in FIGS. 5 and 6. The slings preferably measure 12" from the inferior to the superior border and correspond to the inferior-superior dimensions of the lateral plates 104, 106. For a prototype which has actually been reduced to practice, two slings were prepared. The first sling 102, shown in FIG. 6, measures 20" from left to right lateral border, and will fit most adults. The second sling 102, as shown in FIG. 5, will fit larger to obese adults and measures 25". Cordura was used in the prototype. At preferably five points along each lateral side of the sling 102 straps 110a–110e are used to connect the sling 102 with each of the lateral plates 104, 106. These straps 110a–110e are adjustable in length so that each sling 102 has a wide range of left to right lateral dimensions. In a preferred implementation, one strap 110a is placed at the antero-superior corner of the sling 102, and a second 110e at the antero-inferior corner. Preferably, three additional straps 110b–110d are attached along the lateral edge of the sling, preferably at 3, 6, and 9 inches from the inferior edge of the sling 102. It is important to note that the part of the sling 102 which contacts the patient's skin has no seams or folds so that skin breakdown is minimized. On most adults the sling 102 and corresponding lateral plates 104, 106 extend inferiorly to superiorly from the buttock crease below the ischium to iliac crest which is located approximately in alignment with the third or fourth lumbar vertebral body.

As discussed above, the semi-rigid pelvic compression splint 100 of the present invention comprises two lateral splinting plates 104, 106. The lateral plates 104, 106 perform a key function of the semi-rigid pelvic compression splint 100 by conferring anterior-posterior rigidity. This rigidity allows the semi-rigid pelvic compression splint 100 to be engaged without greatly compromising visual and operative access to the anterior abdominopelvic wall and genital area (discussed in more detail below). Preferably, they measure 12" inferior to superior by 11" posterior to anterior (i.e. 11" in anterior height). The 11" anterior height is sufficient to clear the anterior abdominal wall of small, medium and large non-obese persons. For obese patients, it is possible to make plates 104, 106 with greater anterior height to accommodate an especially protuberant abdomen. Because the anterior height of the bony pelvis does not change as much as abdominal girth in the obese, the rest of the plate would not be likely to need very significant alteration. The plates 104, 106 are preferably constructed of medical-grade plastic, such as that used in other pre-fabricated splints. Acrylic is preferred because it is inexpensive, strong, easy to work with, and readily available. Alternatively, it is possible that this rigidity could be provided using different materials, such as other types of plastic, or especially strong form-retaining inflatable cushions or inflatable/foam hybrids.

The lateral plates 104, 106 on the prototype employ ¼ thick acrylic reinforced in the posterior-anterior plane by three ⅛"×1.25"×11" ribs (not shown). These materials provide adequate splinting support and compression of the pelvis. The firm foam inner shell cushions 112, 114, inflatable air bladders 116, 118 and adjustable strap system 108a–108c and 110a–110e are attached to the lateral plates 104, 106, and combine to allow the splint 100 to conform to the individual patient's lateral pelvic contours.

On each lateral plate 104, 106 are preferably five attachment points corresponding to the five sling straps 110a–110e. Attachment point one is preferably located ¾" superior to the inferior edge of the sling 102 and ¾ inches posterior to the anterior edge. Attachment point five is located ¾ inches to the superior edge of the sling 102 and at the same anterior height as attachment point one. At these attachment points female snap lock pieces are preferably mounted, however, other mounting means may be used. They attach superior and inferior aspects of the sling 102 to the lateral plates 104, 106, thereby stabilizing the sling 102 and preventing significant inferior-superior translation of the sling 102 on the plates 104, 106. Attachment points 2, 3, and 4 are preferably located three, six and nines inches superior to the inferior edge of the lateral plates 104, 106, respectively. They all preferably extend from ¾" to 1.5" inferior to the anterior edge of the plates 104, 106 (i.e. also at the anterior "top" of the plates 104, 106). At these attachment points complete compressive circuits are mounted. These circuits preferably consist of the following components:

Female snap locks on both right and left that attach to the male snap locks on sling straps two through four (110b–110d).

Anterior straps 108a–108c mounted on the left lateral plate 106. These straps 108a–108c are oriented toward the right lateral plate 104. At the end of these straps 108a–108c are male snap-lock pieces with buckles that allow the strap length to be adjusted.

Mating female ends of the snap locks on the right lateral plate 104. These point toward the left lateral plate 106 and meet with the incoming straps from that plate 106.

The combination of posteriorly-based medially-directed compression from the sling 102 and anteriorly-based medially directed compression from the anterior straps 108a–108c balance out to create complete medially-directed compression circuits in inferior-superior alignment with attachment points two through four. These are preferably located 3, 6 and 9 inches from the right and left inferior edges of the splint 100 and are spaced to provide the strongest medially-directed compression forces at the sacroiliac and pubic symphysis joints of the pelvis. Disruption of these joints is the most common cause of life-threatening pelvic fractures. There are no compression circuits superior to the fourth strap because they would interfere with access to the anterior abdomen and pelvis and provide unnecessary and potentially undesirable compression of the iliac wings superior to the SI joint. The lack of compression circuits below the third strap is intended to avoid external leveraging of the hip by the femur and to avoid unnecessary interference with access to the ano-genital area. The plates 104, 106 and sling 102 continue beyond the fourth and second straps to add stability to the splint 100.

Figure 3:
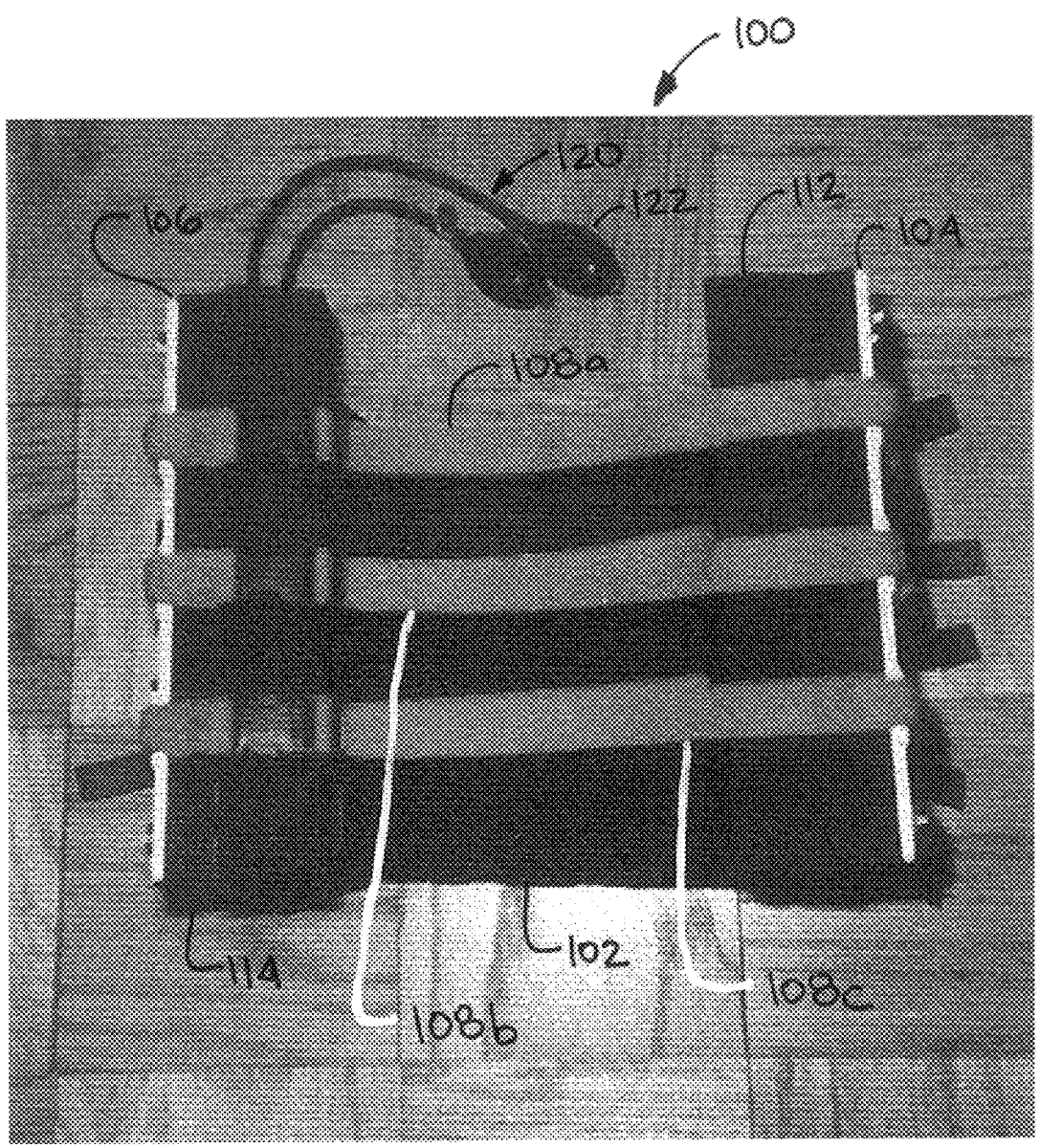
FIG. 3 illustrates a top view of the semi-rigid pelvic compression splint of FIG. 2.
Figure 4:
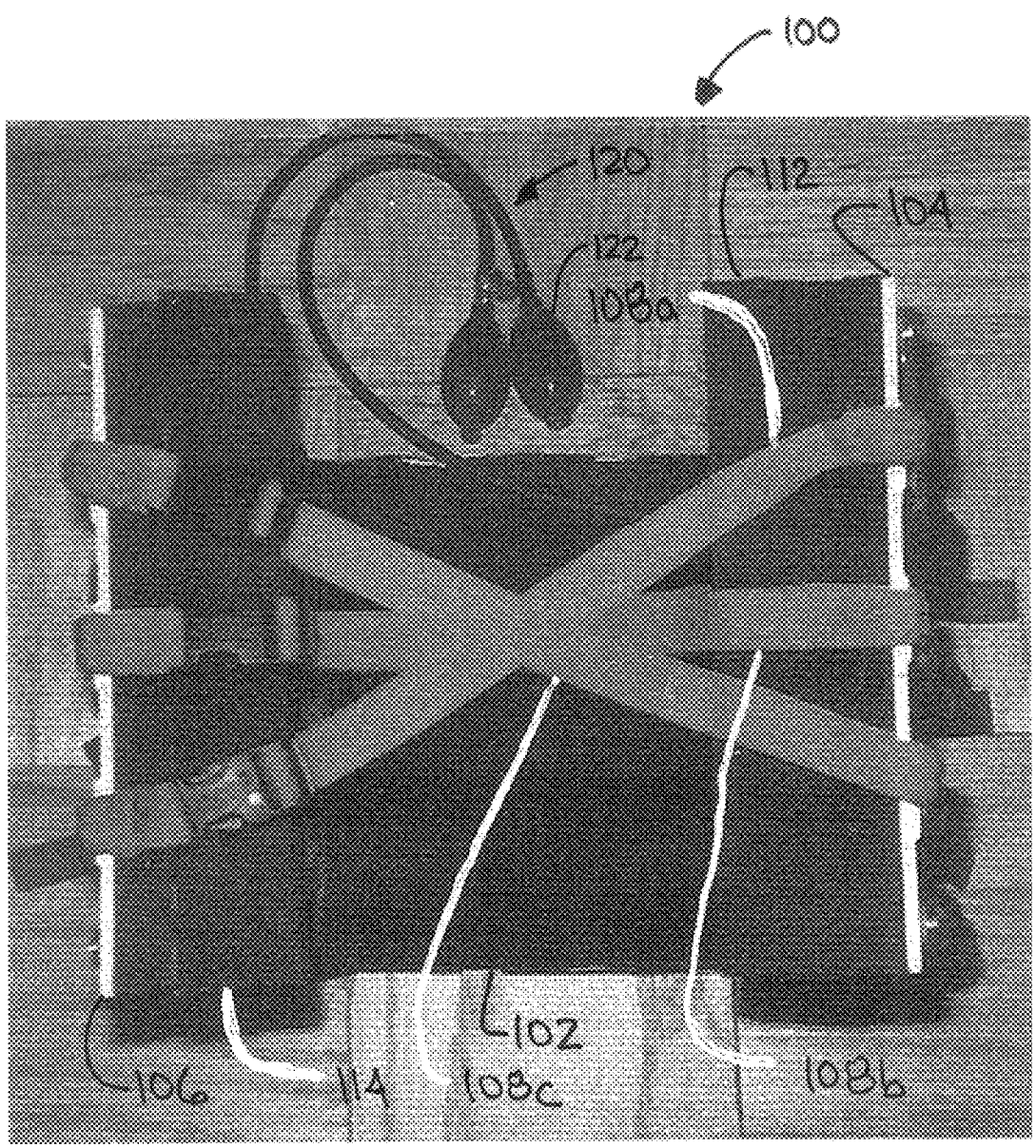
FIG. 4 illustrates a top view of the semi-rigid pelvic compression splint having an alternative strapping configuration.
Figure 5:
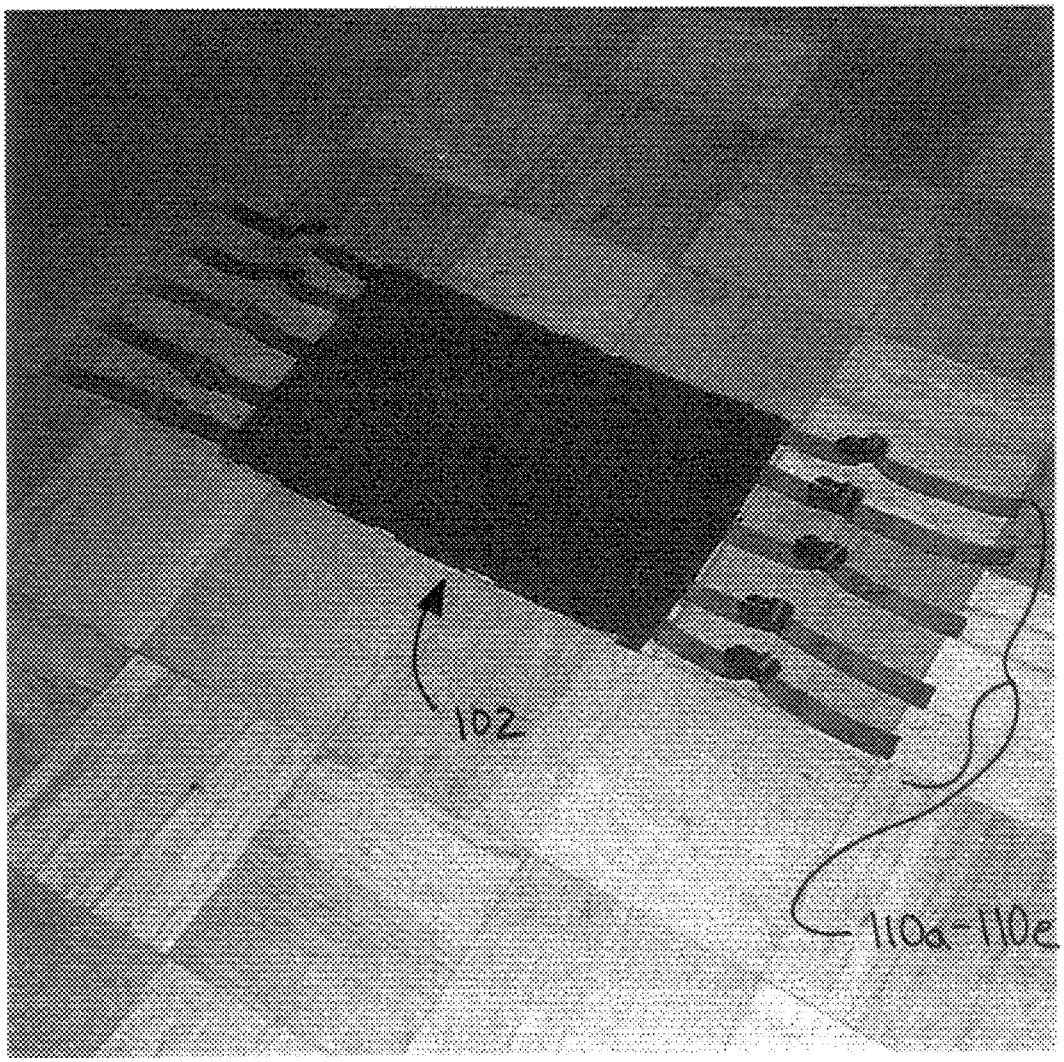
FIG. 5 illustrates a perspective view of an external aspect of a 25" sling used in the semi-rigid pelvic compression splint of the present invention.
Figure 6:
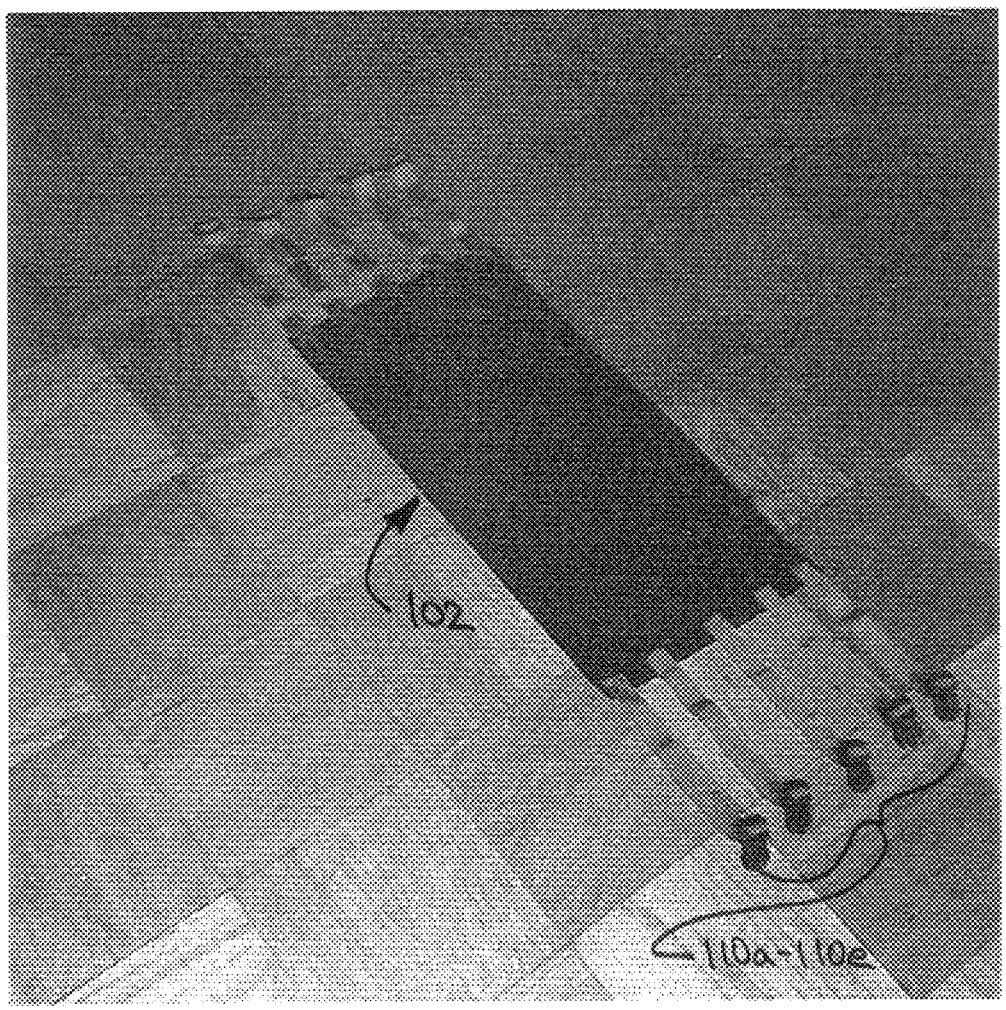
FIG. 6 illustrates a perspective view of an internal aspect of a 20" sling used in the semi-rigid pelvic compression splint of the present invention.

Preferably, the anterior straps 108a–108c and corresponding female snap lock pieces swivel on D-rings, which may be fastened straight across the two lateral plates 104, 106 as is shown in FIG. 3 or placed in an "X" formation shown in FIG. 4. The "X" formation could be used in a patient who is particularly obese and in whom compression at the most superior aspect of the splint 100 is desired (e.g. SI instability). In the obese patient with a protuberant abdomen, attaching the outer anterior straps and snap locks directly across could cause unwanted anterior (posteriorly directed) compression of the anterior abdominal wall. An "X" formation permits a lateral (medially-directed) compressive force vector at the superior aspect of the splint 100 and ensures that the straps do not overlay the most protuberant part of the abdomen (in most obese people the abdomen is most prominent around the level of the anterior superior iliac crest). The "X" formation may also provide some compression along the inferior-superior axis of the pelvis.

Preferably, on the external surface of each lateral plate 104, 106 are three bonded acrylic ribs (not shown) oriented posterio-anteriorly (bottom to top). These ribs are preferably ⅛" thick and 1.25 inches wide (inferior to superior) and span the entire anterior height of the plates 104, 106. The ribs are preferably aligned with the three inner sling straps and attachment points.

The ribs increase rigidity of the posterior-anterior axis of the plates 104, 106 so that the plates 104, 106 do not bow over the abdomen as the anterior straps are attached and the air bladders 112, 114 inflated. Bowing would alter the compression vector of the device, cause compression of the soft anterior wall of the abdomen and pelvis, and limit access and visualization of the area.

The ribs also form a reinforcing skeleton that strengthens the splint 100 at the three complete compression circuits. As noted above, ribs are preferably located at each of these circuits.

A firm, sealed (washable) synthetic or neoprene foam cushion 112, 114 is preferably bonded to the internal surface of each lateral plate 104, 106. AS shown clearly in FIG. 8, each foam cushion 112, 114 preferably forms a shallow C-shape in cross-section to conform to the shape of the pelvis. The purpose of the foam cushions 112, 114 is to fit the lateral plates 104, 106 to the external contours of the pelvis, thereby optimizing compression vectors. By padding the device they also decrease the likelihood of skin complications. The cushions 112, 114 preferably cover the entire internal surface of each plate 104, 106. Although the c-shape is shown curved in FIG. 8 for simplicity, a preferred shape is as follows. The base thickness of the cushions 112, 114 (at the inner concavity of the C) is preferably 1 inch. At the posterior edge of the cushions 112, 114 a wedge preferably extends 2 extra inches medially and tapers back to baseline thickness two inches (in anterior height) up the splint 100, forming a triangular shape. Another wedge tapers out at a point preferably 7 inches in anterior height for the posterior edge. This wedge preferably extends medially 2 inches from the baseline thickness of each foam cushion 112, 114. It will reach this medial distance at 9 inches in anterior height. At that point each foam cushion 112, 114 remains at a constant 3 inches in thickness as it proceeds to the anterior edge of the plate.

Preferably, on the foam lined medial side of each lateral plate 104, 106 are inflatable nylon covered rubber compartments (referred to as air bladders) 116, 118. For convenience, large adult blood pressure cuffs were used in the prototype, however, a manufactured device would preferably use customized synthetic or natural rubber compartments. The air bladders 116, 118 provide strong compression and close approximation of the splint 100 to the individual patient's external pelvic contours. The simplest arrangement would be similar to the large blood pressure cuffs employed in the prototypes and would have a single inflatable cushion housed in a nylon shell. In the prototype these are fastened directly to the foam-lined internal surface of each splint using Velcro so that it is possible to remove the cuffs for maintenance and cleaning. The air bladders 116, 118 extend from the postero-medial to antero-medial ends of the "C" of the cushions 112, 114. Using the inflatable compartment mounted in this fashion, the dominant compression vector is lateral to medial (medially-directed). The wedge-mounted parts of the compartment ("arms of the C shaped cushions 112, 114") provide some anterior and posterior support. Because the shallow C-shape of the cushions 112, 114 and air bladders 116, 118 provide form-fitting "customized" compression along the entire span of the lateral bony pelvis, both anterior and posterior fractures (e.g. "open book" PS fractures and SI disruptions) are compressed and stabilized. Each of the air bladders 116, 118 are equipped with a pump and valve system 120 designed to prevent passive air leak and to allow easy inflation with a hand or foot operated pump. In the prototype this system employs a simple blood pressure squeeze bulb 122.

Optional inflatable air bladder 116, 118 designs can also be utilized. It is possible to make several more complex variations of the inflatable air bladder. It may be molded into a sharper C-shape or be ribbed so that it conforms more closely to the pelvis. Alternatively, two or more compartments may be housed in each nylon shell so that compression in each compartment may be changed. If longer term use of the splint is necessary, a system of alternatively inflating compression compartments (e.g. such as is currently employed in Venodyne deep venous prophylaxis systems) could be used so that skin breakdown is minimized. The timing of inflation and release of these compartments would have to be adjusted so that even pelvic compression was maintained. A more significant change would be to employ a form fitting inflatable cushion that is molded in the shape of the C-shaped foam skeleton, and which would replace part or all of the neoprene foam and the simple rectangular inflatable compartments of this prototype. Such a component, especially if available in a material that retained some shape when partially or completely deflated, could be very useful, as it may allow the splint 100 to fit more closely, be easier to place, and more stable on the patient. Nonetheless, it must be emphasized that the C-shaped foam cushions 112, 114 and inflatable air bladder 116, 118 on the present prototype are relatively inexpensive, effective, and easy to assemble and adjust. There is already significant adjustability built into the splint 100 with this system. By distributing volume to lower pressure areas even simple single inflatable compartments customize splint shape and compression to the needs of the individual patient.

As discussed above, obese persons may require a splint with greater anterior height (e.g. 12"). This may be expected to change the dominant compression vector by lengthening the torque arm for the pull by the anterior trans-abdominal straps 108a–108c. Fortunately this effect can be attenuated by increasing the pulling force of the posterior sling by increasing the tension on the straps connecting it to the lateral plate 110a–110e.

As discussed above, the semi-rigid pelvic compression splint 100 of the present invention further comprises an attachment system. The semi-rigid pelvic compression splint employs a male/female snap-lock and nylon webbing length-adjustable system for attaching the posterior sling 102 to the lateral plates 104, 106 and the lateral plates 104, 106 to each other. Similar systems are commonly found on life vests, trauma backboards, luggage and other equipment in which adjustability, secure closure, and simple engagement and disengagement are necessary. The strap and snap-lock system holds the splint 100 together as a unit. Because the snap locks allow easy changes in the length of the straps, size can be easily adjusted, as can the relative strengths of the posteriorly and anteriorly-based medially-directed compression vectors. Alternatively, a roller (not shown) could be used instead of straps to provide adjustability in the length of the posterior sling. The anterior straps 108a–108c balance necessary strength with as little interference in anterior abdominal and pelvic visibility and access as possible, and can be placed in an X-formation as shown in FIG. 4. The nylon webbing straps and plastic snap locks used on the prototype are one inch in width.

The semi-rigid pelvic compression splint 100 of the present invention optionally further comprises non-sling and strap compression systems. The fastening and compression system described in the sections above, while being a big improvement over the prior art, have some disadvantages. First, the parts of the buttock and back covered by the posterior sling 102 will not be directly seen once the device is placed on the patient. It is therefore imperative that the paramedic, nurse, emergency physician or surgeon who first places the device carefully record any visible or palpable injuries to the buttocks, buttock crease and sacral area. Because some clinicians may wish to leave the semi-rigid pelvic compression splint 100 in place during laparotomy and may wish to have nothing overlying the anterior abdomino-pelvic wall one, and possibly more of the following external compression systems could also be used. These could increase the versatility of the semi-rigid pelvic compression splint 100.

For in-hospital transfer to the systems described below the design of the lateral plates 104, 106 need not be modified. Very shallow 3-sided plates attached to long adjustable bolts which are in turn attached to an externally fixed device could fit over each rib and be used to directly compress the lateral plates (i.e. like the palm of an extended hand pushing on a door or wall, in which the door is lateral plate/rib, the hand is the shallow plate, the bolt is the extended arm, and the shoulder and body is the externally fixed device).

Alternatively, there are numerous minor modifications that could facilitate compression using an externally fixed device. One such modification is to mold four ridges to the inferior and superior walls of the left and right ribs. The ridges would be as thick as the corresponding rib and would be located on each side of the rib at about 2.75 and about 6.25 inches in anterior height from the posterior edge of the lateral plate 104, 106. The rectangular area framed by these ridges would form a base that limits posterior-anterior translation of three-sided shallow plate along each rib. The anterior height of these ridges is chosen so medially-directed compression from the external system would be centered over the posterior to anterior span of the lateral bony pelvis. Other design options for in-hospital conversion to external attachment/compressive systems include molding square or circular shaped depressions between the ribs. These female molds would accept the corresponding male part of the external attachment system. It may even be possible to use Velcro to achieve the same purpose because the compressive force vector would be against and not across or away from the Velcro.

Because no modification of the lateral plates are needed, designs discussed below will assume plates 104, 106 are left unmodified.

Once the patient has been transported to the ED, rolled by the trauma team and able to be maintained in the supine position for a long period, the patient is transferred on the EMS backboard (with the sling/splint left in place) to a specialized backboard with plastic blocks designed to provide a fulcrum for medially directed compression of the splinting plates. This backboard would have to provide adequate padding so that the patient could be placed on it for relatively long periods without causing significantly more patient discomfort of skin breakdown than an emergency department, OR, or recovery room gurney. The specialized backboard would be of standard width, except in the pelvic region, where it would be widened to accommodate the patient, the semi-rigid pelvic compression splint, two lateral compression blocks and area for adjustment of the compression mechanism (approximately 30 inches). The padding would extend outward to encompass the shape of a standard backboard, but would not extend over the area where the compression blocks would be mounted. At the midpoint of the pelvic area (corresponding with attachment point 3 at each side would be centered to plastic blocks (BEA-L and BEA-R) rising 9 inches in anterior height from the base of the backboard (the patient and splint, lying on about 2.5 inches of firm padding, will be about two inches over the plastic base of the backboard). The inferior-superior width of these blocks will be 10 inches and the internal-external width will be 3 inches (i.e. wide enough strength to compress the pelvis). Three machined holes 1 inch in diameter would be centered 6.5 inches from the posterior base of each block (H-2 L or R, H-3L or R and H-4L or R from inferior to superior) and would correspond inferiorly to superiorly to lateral plate attachment points 2, 3 and 4.

The holes would have threading to allow them to accept a bolt and would be metal lined if necessary. Through each hole would pass a 1 inch diameter metal (or high strength plastic) bolt measuring 8 inches in length (B-2L or R, B-3L or R, B-4L or R). On the external side of the bolts would be a large grip to allow adequate torque for effective hand tightening and securing nuts (NE-2L or R, NI-3, NI-4). Internal to the blocks the bolts would thread through a second hand-tightened securing nut (NI-2L or R, NI-3L or R, NI-4L or R), and have a 3-sided shallow plate (SP-2 through 4, L and R) mounted to the internal end. The shallow plate would extend 1.5 inches from the center of the bolt anteriorly and posteriorly and would extend approximately 0.80 inches inferiorly and superiorly The shallow plates are designed to fit over the ribs on the splint.

Once the patient is on the backboard the B-2L bolt is tightened until the shallow plate SP-2L overrides rib R2-L. Sling straps SL-1L and SL-2L are then released and the sling is folded away from rib R-2L. Bolt B-2L is then tightened until the shallow plate SP-2L fits over the rib R-2L between the ridges, and provides close compression. The lock nuts NE-2L and NI-2L are then tightened down to each side of the block to lock the device. This procedure is continued at R-4R, then R-4L, and then R-2R. Once the "corners" of the sling are disengaged and replaced with the external compression system the central straps SL-3L and R are disengaged, and B-3L and R are tightened down. Once all compression is through BEA-L and the sling straps will be laying on the backboard between the lateral plates and the compression blocks, and the sling can be carefully pulled out from under the patient and the lateral plates (or it can be left under the patient). Using this transfer process there is no interruption of lateral pelvic compression, the patient can be easily transported, and the entire abdomen is fully accessible for laparotomy.

The patient can be transferred from the standard EMS backboard by lifting the EMS backboard over the specialized backboard and placing the patient and EMS backboard on the specialized backboard. The patient is then rolled laterally with careful "in-line" axial traction and the EMS backboard is slid out from under the patient and over the plastic block (BEA) on the side away from which the patient is rolled. After the patient's back is examined by the trauma team, he or she is rolled to his or her back in "in-line" manual traction.

An alternate way to make this transfer is to design the specialized backboard so that blocks BEA-R or L can be separated from the specialized backboard. This would allow the patient in the semi-rigid pelvic compression splint and on the standard backboard to be simply slid laterally over to the specialized backboard, as is now done when transferring trauma patients from EMS to ED stretchers. The patient is then rolled with "in-line" manual traction toward the side in which the BEA remains attached to the specialized backboard, and the EMS-type backboard is slid out in the usual manner. The patient's back is examined and he or she is log-rolled back to supine position and aligned correctly on the new backboard. At that point the compression block is replaced and the external compression system engaged as above.

A detachable block for use with the semi-rigid pelvic compression splint can be designed as follows. The block is lengthened in the inferior-superior axis to 14 inches. On the portion of the backboard corresponding with the desired location of the plastic blocks is a system of five holes. Three square holes (SH-2 L or R, SH-3, SH-4) one inch in length and width are located on the backboard directly under the corresponding bolt holes in the overlying block (i.e. SH-3 in the center and SH-2 and 4 located three inches inferior and superior to the central hole). Holes SH-1 and SH-5 are located 6 inches inferior to and superior to SH-3, respectively. SH-1 and SH-5 are round, metal lined, and have a half inch deep square shaped countersunk metal lined depression on the bottom (posterior aspect) of the board.

The plastic block itself would have 3 square pegs (SP2, and 4L or R) extending one inch down (posteriorly from the block directly under bolt holes H-2, 3 and 4). Round, one inch diameter holes (H-1 and H-5) would be drilled from anterior to posterior in the internal/external midline of the block six inches inferior and superior to H-3. On the anterior surface of the blocks, a metal washer would be molded into the plastic at the openings of H-1 and H-2. The block would be placed on the backboard so the square pegs and holes fit together. Foot long bolts (BF-1, and BF-5) with a ½ wide square head would then be pushed up through SH-1 and H-1 and SH-5 and H-5 and held in place. A large grip hand-tightened nut (NV-1L or R, NV-2L or R) would be threaded over and tightened down flush to the metal washers molded into the plastic blocks. At that point the plastic blocks would be secured to the background and the external compression system could be engaged.

Further refinement of this system could include blocks that adjust in anterior height, using any number of existing mechanical technologies—such as rubber pads that go between board and block to increase the anterior height of the blocks or height adjustable removable clamps that attach to the backboard itself and the blocks.

A simple flat board (with height adjusted blocks) that slides under a standard stretcher mattress could also be used. This system has no advantages over the specialized backboard system, and would be more difficult to employ because of the differences in stretcher design. Such a board could also be placed over a standard stretcher and the standard EMS type backboard could be placed over that. The obvious disadvantage of this is that an EMS backboard is hard, and therefore injurious to skin and not well-tolerated by patients. Making a small padded buttock and sacral plate and pad on which block is feasible, but undesirable, because any system strong and well padded enough would lift the buttocks too much (relative to the rest of the body) and increase the risk of pressure ulcers and loss of spinal alignment.

It would be advantageous to manufacture clamps that allow the external compression blocks to be mounted on a gurney/stretcher or OR table. Several variations are possible. An anterior-height adjustable clamp for stretchers could be mounted to the underside of compression blocks. This would allow the blocks to be mounted to a stretcher platform (CLAMP-1). A modified clamp could be made to fit the side rails of an OR table (CLAMP-2). There are two major disadvantages that make such system less useful than specialized backboard. First, the patient would need to be transferred back to the sling and snap lock mechanism any time transfer to another bed or stretcher (e.g. to a CT or OR table) was necessary. This would slow down the early resuscitation and diagnosis process. A second disadvantage is that the technology would be dependent on the strength and stability of various stretchers and OR tables. This may cause product failure. Manufacturing modified stretchers or OR platforms would obviously be impractical and a great deal more expensive than the specialized backboard described above.

External fixation frames that fit over the lateral plates could be used as an alternative for providing compression. These devices could be designed in many ways. They could be manufactured to lie in low profile over the patient's legs and out of the way of the critical abdomino-pelvic area. They would compress the lateral plates using the same 3-sided female compression units that are described above. Frames that resembled currently used external fixation and "C" clamps could also be used. These would employ the same 3-sided units described above in place of the invasive indwelling pins that the conventional external fixation devices use. Two or three of these external fixation-type frames could be used to provide pelvic compression, and be swivelled out of the way of the abdomen. Unfortunately, frame systems are likely to be very difficult to use with a non-invasive splint. Frames would have a high center of gravity and would be likely to increase the instability of the lateral plates. Designs which have posterior support and a lower center of gravity (such as the basic sling and strap splint, as well as the other designs in which external compression blocks are mounted on a relatively fixed surface) are more feasible with lateral plates that lack invasive pins to completely fix the plates or frame to the patient. Adding "feet", or bottom weighting the clamps to stabilize them posteriorly would be complex because stretcher and table sizes vary, and because such frames would be unwieldy in transport.

Of all the non-sling and strap compression mechanisms described, the specialized backboard is the most feasible for in-hospital conversion from the sling and strap mechanism to a more fixed device that leaves the entire abdomen and pelvis open anteriorly. The specialized backboard is the most stable, and allows the patient to be transported from ED stretcher to CT or OR table with ease (the entire backboard is lifted with the patient and placed on the new care surface). It is also a relatively simple and mechanically strong system.

The sling and strap system of the splint 100 has significant advantages over any system described above or in present use. It would be relatively cheap, which would allow its widespread use by hospitals, EMS and other provider systems. It is relatively compact, and it can be easily stored in an ambulance or emergency department trauma resuscitation room. It is the only product described above that is adaptable to all the currently used major trauma transport and care platforms. A patient in the semi-rigid pelvic compression splint 100 could be placed on a standard EMS backboard, transferred to an ED stretcher, rolled repeatedly for re-examination of the patient's back, and moved to a CT or OR table. None of these position changes would require removal or adjustment of the splint 100. Most important is that the sling 102 is easy-to set-up. This, and the versatility described above makes the device a timesaver. Although trauma resuscitation is supposed to occur rapidly, experience in level-1 trauma centers have shown that performing all the procedures inherent in resuscitating trauma patients takes much longer than expected. Therefore, rapid deployment in the field of ED is a critical attribute for any technique or device added to the regular care of the injured. Another advantage to mention is that the splint 100 has no metal parts in contact with the patient and is therefore unlikely to cause significant interference with CT images.

Although the semi-rigid pelvic compression splint 100 of the present invention has some disadvantages, they can be easily minimized.

As noted above, the buttock crease, buttocks and sacral area would be carefully examined before application of the splint 100 in the field or at the hospital. Later examiners could reexamine this area by palpating through the posterior sling component of splint 100. The ano-genital area would remain accessible with the splint 100 in place. If early pelvic films did not reveal a significant fracture the splint 100 could be removed. If such films did reveal a significant fracture, the advantages of leaving the splint 100 in place would significantly outweigh the benefit provided by re-visualizing the buttock and skin surface anatomy. Finally, all other devices mentioned above prevent easy provider examination of this region.

Interference with the sterile field for laparotomy could be minimized by placing the anterior straps 108a–108c in the "X" position and draping the device. As noted above, a key benefit of the semi-rigid pelvic compression splint 100 is that even with the anterior straps 108a–108c in standard formation, the lower abdomen and pelvis would be visible and palpable, and the entire abdomen above the umbilicus would be completely open. Placing the anterior straps 108a–108c in X-formation would add an open V-shaped area over the lower abdomen (extending to the pubic symphysis) to the operative field.

Lower level trauma centers and EMS companies may find it a desirable means for performing transfer of a pelvic fracture patient to a distant level one trauma center after initial assessment and stabilization is performed. Again, the versatility, low-cost, simplicity, and speed of deployment make the semi-rigid pelvic compression splint 100 of the present invention with the sling and strap likely to become a very popular, effective and widely used product with potential to become standard equipment for EMS systems, ED's and trauma units throughout the U.S. and other countries.

Variations deriving from the "basic concept" as being possible include but are not limited to:
- Substituting Velcro for snap locks, or changing male and female snap-locks or vice-versa;
- Using different materials than those specified above;
- Making small changes in design or concept: e.g. Substituting the foam internal skeleton or inflatable compartments for other means, reversing their positions, changing the conformation or dimensions of the cushions, air bladders, plates, sling, or the like;
- Offering alternative external compression system designs not identical but similar in concept to those described above;
- Making any product that is significantly derived from the "basic concept" and any possible related or secondary concepts described above.

Although the MAST and external frame systems have great benefits, they are not widely used because of their disadvantages, which mainly consist of limiting the examination of the patient, delaying other effective treatment modalities, causing device-specific skin, lung and infectious complications, and requiring extra time or expertise in early trauma management. Because The semi-rigid pelvic compression splint 100 of the present invention has the potential to provide the same benefits as these devices with less medical, temporal and economic costs, its widespread use is likely, including in military settings, rural and community health systems and even developing nations. The design of the splint 100 is consistent with the trend over the last thirty years to decrease the level of invasiveness in trauma care. This trend has been humanistic and benefitted individual patients. It has also improved the overall effectiveness of the nationwide trauma system by distributing the ability to perform important life-saving functions from specialists to EMTs and Paramedics, ED Physicians and Nurses, and General Surgeons.

Descriptions of dimensions and directions herein employ standard anatomical terminology, including lateral, medial, anterior, posterior, inferior, and superior. These terms relate to a given object's position in reference to the supine patient's body (i.e. objects relatively closer to the head are superior to objects closer to the feet, and objects relatively closer to the abdominal surface are anterior to those that are closer to the patient's back). Common terms such as "above", "below", "over", etc. are also used for convenience in a conventional non-anatomic sense and refer to the position of objects in space.

Size specifications for the semi-rigid pelvic compression splint 100 of the present invention are intended to provide guidelines for a "medium-sized" final product that will fit most adults. They were obtained by measuring the pelvic dimensions of several medium-sized males and by reviewing male and female cross-sectional pelvic anatomy in a text-book with a scale ruler.

Specifications of the composition of the semi-rigid pelvic compression splint 100 of the present invention are based on a familiarity with other emergency medical products, local availability of materials, and the facility for working with these materials. It should be apparent to those skilled in the art that different materials may be chosen to construct the semi-rigid pelvic compression splint 100 without departing from the scope or spirit of the present invention.

The semi-rigid pelvic compression splint 100 of the present invention will stabilize and provide lateral (medially directed) compression to the entire fractured pelvis in trauma which has the following advantages over the prior art:

Compression/stabilization reduces pelvic volume and displacement of fractured bones, thereby tamponading life-threatening bleeding from pelvic veins and cancellous bony fragments;

Compression/stabilization protects the pelvis from further of repeated injury during pre-hospital transport, emergency department resuscitation, and the early inpatient phase in which diagnostic testing and repair of other serious injuries typically occur prior to definitive repair of the pelvis. Pelvic movement can cause re-bleeding by dislodging clots, shifting bone fragments, and opening previously tamponaded hematomas;

Stabilization of any fracture is the most effective way to increase patient comfort. This is particularly important during the multiple patient movements and manipulations that occur during the pre-hospital and early hospital period.

An extremely important advantage of the semi-rigid pelvic compression splint of the present invention is that there is no direct splint-derived compression vector centered on the bony landmarks that mark any of the major operative approaches to the traumatized pubic symphysis or sacroiliac joint. This is a marked distinction to the MAST pants (or any other non-invasive device with significant anterior-posterior compression), which cause skin breakdown directly over these landmarks. It is also important to note that the invasive external devices minimize skin breakdowns over a large area, but cause significant pintract infections that may complicate later operative management.

The semi-rigid pelvic compression splint 100 of the present invention advantage of not requiring specially trained experts should be re-emphasized. As noted above, this is critical in the pre-hospital and community hospital setting. Even at the level one trauma center, reducing the need for multiple specialists and procedures early in the resuscitation of polytrauma patients is advantageous because trauma management in such centers is already plagued by difficulties with resuscitation area crowd control and prioritization of time consuming activities. Although it is mandatory to have orthopedic consultation early in pelvic fracture management, it is often not feasible to have a team perform a relatively complicated and space occupying procedure requiring meticulous antiseptic preparation (relative to placing on IV, chest tube, endo-tracheal tube, Foley catheter, or even diagnostic peritoneal lavage) in the early resuscitation and management of multiply-injured patients.

The lack of need to place surgical pins with the semi-rigid pelvic compression splint 100 of the present invention saves time and speeds the patients arrival to CT scan, laparotomy, or pelvic angiography. Placing the splint can be done in the field by EMS, or very quickly and without advanced training by trauma team members. The placement of the device advanced training by trauma team members. The placement of the device would be relatively "free"—it would combine the benefits of the MAST pants, External Fixator, C-Clamp, and Pelvic Stabilizer without causing the problems and complications that hinder the use of each.

While there has been shown and described what is considered to be preferred embodiments of the invention, it will, of course, be understood that various modifications and changes in form or detail could readily be made without departing from the spirit of the invention.

What is claimed is:

1. A pelvic compression splint for splinting support and compression of the pelvis, the pelvic compression splint comprising:
    right and left unitary rigid plates configured to be positioned on the right and left sides, respectively, of the pelvis and projecting anteriorly above the abdomen without contacting the abdomen, the right and left unitary rigid plates each substantially covering an entirety of the right and left sides, of the pelvis, respectively;

right and left cushions positioned between the right and left plates, respectively, and the right and left side of the pelvis; and a support means for supporting the right and left plates and right and left cushions compressively against the right and left sides of the pelvis to reduce pelvic volume and control pelvic hemorrhaging.

2. The pelvic compression splint of claim 1, wherein the right and left cushions further have a concavity to fit the contours of the right and left sides of the pelvis, respectively.

3. The pelvic compression splint of claim 1, wherein at least one of the right and left cushions further comprises an inflatable compartment for applying further and varying compression against the right and left sides of the pelvis.

4. The pelvic compression splint of claim 3, wherein the inflatable compartment further comprises a pump and valve system for pressuring the inflatable compartment and releasing pressure therefrom, respectively.

5. The pelvic compression splint of claim 4, wherein the pump comprises a squeeze bulb connected to the inflatable compartment by a conduit, wherein the valve is disposed within a fluid path of the conduit.

6. The pelvic compression splint of claim 1, wherein the support means comprises a sling fastened at each end to the support plates by a first plurality of straps, the support means further having a fastening means for maintaining the support plates and cushions compressively against the right and left sides of the pelvis.

7. The pelvic compression splint of claim 6, wherein the fastening means comprises a second plurality of straps, each of the second plurality of straps having a fixing means for fixing the straps to each of the support plates.

8. A pelvic compression splint for splinting support and compression of the pelvis, the pelvic compression splint comprising:

right and left unitary rigid plates configured to be positioned on the right and left sides, respectively, of the pelvis and projecting anteriorly above the abdomen without contacting the abdomen, the right and left unitary rigid plates substantially covering an entirety of the right and left sides, respectively, of the pelvis;

right and left cushions positioned between the right and left unitary rigid plates, respectively, and the right and left side of the pelvis; and a sling disposed around the right and left unitary rigid plates for supporting the right and left unitary rigid plates compressively against the right and left sides of the pelvis to reduce pelvic volume and control pelvic hemorrhaging, the sling further having a fastening means for maintaining the right and left unitary rigid plates compressively against the right and left sides of the pelvis, the fastening means comprises two or more straps.

9. A pelvic compression splint for splinting support and compression of the pelvis, the pelvic compression splint comprising:

right and left unitary rigid plates configured to be positioned on the right and left sides, respectively, of the pelvis and projecting anteriorly above the abdomen without contacting the abdomen, the right and left unitary rigid plates substantially covering an entirety of the right and left sides, respectively, of the pelvis;

right and left cushions positioned between the right and left unitary rigid plates, respectively, and the right and left side of the pelvis; and a sling disposed around the right and left unitary rigid plates for supporting the right and left unitary rigid plates compressively against the right and left sides of the pelvis to reduce pelvic volume and control pelvic hemorrhaging, the sling further having a fastening means for maintaining the right and left unitary rigid plates compressively against the right and left sides of the pelvis, the fastening means comprises at least one strap supported anteriorly above the abdomen of the patient by the right and left unitary rigid plates.

* * * * *